Figure 1:
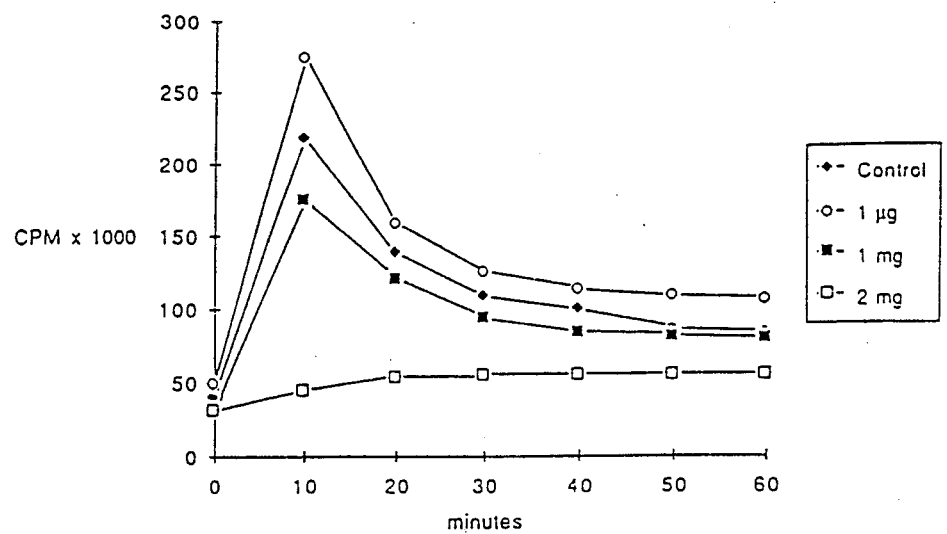

United States Patent [19]

Harrington-Fowler et al.

[11] Patent Number: 4,894,329
[45] Date of Patent: Jan. 16, 1990

[54] METHOD OF ASSAYING THE BIOACTIVITY OF A THYMIC EXTRACT

[75] Inventors: Linda Harrington-Fowler, Medfield; Martin S. Wilder, Amherst, both of Mass.

[73] Assignee: Serono Pharmaceutical Partners, Boston, Mass.

[21] Appl. No.: 19,681

[22] Filed: Feb. 27, 1987

[51] Int. Cl.⁴ ............................................... C12Q 1/02
[52] U.S. Cl. ....................................... 435/29; 436/172
[58] Field of Search .................... 435/29, 810; 436/63, 436/172

[56] References Cited

FOREIGN PATENT DOCUMENTS 0159653 10/1985 European Pat. Off. .

OTHER PUBLICATIONS

Allen et al., *Biochem. Biophys. Research Communic.*, 69, 245–252, 1976.
Coleman et al., *J. Immunol.*, 130, 2195–2199, 1983.
Coleman et al., *J. Immunol*, 133, 3121–3127, 1984.
Mellors et al., *Cell. Immunol.*, 110, 391–399, 1987.
Ippoliti et al., 5th European Immunology Meeting, Istanbul, Turkey, June 1–4, 1982, Abstract.
Herbert et al. (E.D.S.), Dictionary of Immunology, 3rd Ed., Blackwell Scientific Publications, Oxford, 1985, p. 114.

*Primary Examiner*—Robert J. Warden
*Assistant Examiner*—David A. Saunders
*Attorney, Agent, or Firm*—Stephan P. Williams

[57] ABSTRACT

A method of assaying the bioactivity of a thymic extract is disclosed. The disclosed method measures the chemiluminescence of macrophage derived from an immune-deficient mouse after stimulation with the sample thymic extract, phagocytic stimulator, and luminescent detecting solution. A kit suitable for practicing the method is also disclosed.

4 Claims, 1 Drawing Sheet

METHOD OF ASSAYING THE BIOACTIVITY OF A THYMIC EXTRACT

BACKGROUND

The HRS/J mouse is an inbred genetically immuno-deficient strain which carries a mutant gene, hr, located on chromosome 14, linkage group III. Strain HRS/J originated from a cross between a random-bred strain carrying the mutation hr and the BALB/cGn strain and consists of 3 genotypes, hr/hr, hr/+ and +/+. Meier, H., D. D. Myers, and R. J. Hueber, 1969. "Genetic control by the hr-locus of susceptibility and resistance to leukemia." PNAS 63:759 (1969). A severe thymic cortical atrophy observed in homozygous hr/hr mice beginning at about 6 months of age with specific defects of the immune system is indicated by 1) a deficiency in their ability to produce antibody to tetanus toxoid and to respond to graft-vs-host reaction and T cell mitogens; 2) a disproportion of Ly-1,2,3+ and Ly-1+ cells; and, 3) an increased susceptibility to challenge with a syngeneic transplantable leukemia.

Peritoneal macrophages in primary cell culture derived from immuno-deficient HRS/J hairless mice can be employed to measure in a quantitative manner the biological activity of natural and synthetic substances which affect cell-mediated immune function. Spreading and phagocytosis are well characterized means of assessing activation kinetics of the mononuclear phagocyte cell line. Harrington-Fowler L. and Wilder, M. S. "Fate of Listeria monocytogenes in murine peritoneal macrophage subpopulations." Infec. Immun. 35:124:132 (1982). It recently has been demonstrated that the HRS/J homozygotes and heterozygous littermates possess unusual susceptibility to infection with facilitative intracellular parasites such as Candida albicans, Staphylococcus aureus, and Listeria monocytogenes.

Moreover, HRS/J-derived peritoneal macrophages express reduced bactericidal and oxidative activities when compared with mononuclear phagocytes obtained from immune competent mice.

Similar to that employed with the HRS/J macrophage, significant information relative to the diagnosis and treatment response of primary and secondary immunodeficiencies in humans to biological response modifiers may be generated using techniques which measure mononuclear phagocyte activation. The term macrophage as used here refers to all cells of the mononuclear phagocyte lineage, both circulating and localized throughout various tissue/organ systems.

Macrophages possess both anti-microbial and anti-tumor activity. Macrophages are responsible for the induction of response to antigen as well as the expression of cell-mediated immune response to microbial parasites and/or neoplastic cells.

Thymostimulin, a thymic extract also known as TP-1 ®, has been shown to partially restore phagocytosis of latex particles by peripheral blood monocytes from patients with tuberculosis. Ippoliti, F.; DiGiovambalista, A. M.; Ferri, A. M.; Naso, G.; Ottaviani, C.; Spina, A.; Fiorani, C. M.; Arienzo, F; and Florucci, F. "Dysphagocytosis in Pulmonary Tuberculosis and its Partial Restoration by TP-1 ® in Vitro," 5th Eur. Immunol. Mtg., Istambul, Turkey, June 1–4 (1982).

All references cited herein are hereby incorporated by reference.

SUMMARY OF THE INVENTION

The present invention describes utilization of macrophage derived from the genetically immune deficient HRS/J mouse for assaying the bioactivity of thymic extracts.

It has been discovered that thymic hormones will modulate several parameters of the cell-mediated immune response when studied in peritoneal macrophages derived from immunodeficient HRS/J hairless mice. In in vitro experiments using thymostimulin, significant dose dependent facilitation of macrophage spreading was seen at thymostimulin concentration of from 0.1 mg to 1.5 mg per culture. When higher levels of thymic extract are used, spreading levels off at 2.0 mg, by inhibition when greater amounts are used.

Time course studies indicate that thymostimulin incubation affects both the serum-independent early macrophage spreading which develops within one hour as well as the serum-dependent delayed spreading associated with spindle formation characteristic of the activated macrophage. The polypeptide extract was also shown to exhibit variable effects on the respiratory burst. Praincubation of resident macrophages with microgram amounts of thymostimulin results in an augmented luminol-dependent chemiluminescence response while higher levels of thymus extract markedly suppress emission of light in response to opsonized zymosan. Luminol dependent chemiluminescense response of human granulocytes to phagocytic stimulus has been previously described. See Stephens, P., Winston, D. J., and Van Dyke, R., "In vitro evalustion of opsonic and cellular granulocytes function by luminol dependent chemiluminesce: Utility in patients with severe neutrophenia and cellular deficient states," Infect. Immunol. 22.41 (1978) and Godfrey, R. W. and Wilder, M. S., Relationships between oxidative metabolism, macrophage activation, and antilistorial activity. U. Leuko. Biolo. 36:533 (1984).

Averaging the data obtained in representative embodiments, thymostimulin concentration of 1 mg, 0.1 mg, 0.01 mg and 1 ug/culture gave spread cell percentages of 43%, 37%, 16%, and 12%, respectively. These values were obtained using $6 \times 10^5$ macrophages, with spreading determined after 24 hours incubation with the extract. Thus, a direct and concentration dependent effect of HRS/J-derived macrophages in primary cell cultures has been shown.

Advantages of the Invention

The invention has many advantages over present methods of assaying for thymicextracts and derivation thereof in cell mediated immune system. Using samples from HRS/J mice, TP-1 ® can be injected peritoneally into the host to yield, after harvest, quantitative and qualitative increases in macrophage spreading activity. Alternatively, peripheral blood monocytes or lung macrophages may be obtained from immune-deficient humans, established in cell culture, and assayed as described.

If coverslip cultures are used, samples can be obtained at several intervals. They can then be fixed, stained and mounted for quantitation. Since macrophages generally adhere are readily to coverslips, their morphology can be visualized and scored relatively easily. Using color and/or black and white photographs, it is possible to obtain photomicrographs of viable cultures at various incubation times using phase contact microscopy, e.g., a Zeiss Invertoscope.

In addition, the chemiluminescent effects brought on through the release of oxygen intermediates by TP-1 ®-exposed macrophages subjected to phagocytic stimulus, coupled with the technical facility in establishing mononuclear phagocytes in primary cell cultures, should allow for the same-day assay of TP-1 ® bioactivity in macrophages derived from humans and other mammals. The use of optional control, or standard, reagents to assist in the assay procedure will also result in substantial time savings.

These and other advantages and aspects of the invention will become apparent after consideration of the following description of the invention.

DESCRIPTION OF THE INVENTION

The invention is concerned with a process of the in vitro assay of . immune deficient conditions. The process involves an assay technique in which the presence of an immune, deficiency is detected and/or monitored visually based upon the response of a suitable macrophage exposed to a thymic hormone.

THE DRAWING

FIG. 1 shows the effect of various concentrations of TP-1 on chemoluminescence, expressed as (CPM)×1000 versus time (in minutes). The data was obtained after the addition of 0.5 ml. opsonized zymcsan (15mg/ml).

Thymic Extracts

Thymic extracts are polypeptides which are obtained from the lymphoid organ, the thymus. Thymic sources may be human. However, cost considerations generally dictate that they be of animal origin.

Useful thymic extracts include thymostimulin, thymosin fraction 5, porcine thymic hormone, thymic factor X, leucotrofina, thymosin$_1$, C-terminal fragment of T$\alpha_1$, N-terminal fragment of T$\alpha_1$, prothymosin $\alpha$, thymosin $\beta_4$, $\beta_1$ peptide, thymopentin, thymulin, kidney fraction 5, serum thymic factor, thymic humoral factor, and the like. Thymostimulin is preferred. Mixtures are operable.

One preferred type of substance for use in the invention is thymostimulin, a partially purified bovine thymic preparation (Istituto Farmacologico Serono, Rome, Italy). Thymostimulin consists of approximately 60 polypeptides with molecular weight of less than 12,000 and is prepared by extraction with ammonium acetate, precipitation with ammonium sulfate, ultra-centrifugation and gel filtration. On polyacrylamide gel electrophoresis (pH 8.3), thymostimulin shows two main characteristic bands with an Rf of 0.22 and 0.42. Thymostimulin promotes several surface characteristics and intracellular events of thymic-derived (T) lymphocytes, including increased T cell maturation and proliferation and augmented.

$\gamma$-interferon and interleukin-2 production. This immune enhancing agent has shown clinical efficacy in primary and secondary immune deficiencies with/without viremia and increases the number of circulating T lymphocyte circulating subset in immunosuppressed patients.

The amounts of thymic extract employed in the invention will range from about 1 pg to about 5.0 mg per $10^5$ primary culture consisting of approximately $1 \times 10^5$ macrophages. Preferred levels of use are from about 1 ug to about 2.0 mg per culture. Since the spreading and chemiluminescent effects are concentration or dose related, the use of a sequence of varying concentration can be employed to monitor bioactivity. Concentration levels of incubation of thymic peptide utilized in assessment of macrophage spreading may be kept constant or varied. When varied, a typical sequence for increasing levels will be 0.1, 0.5, 1.0 and 1.5 mg/culture.

Thus, when chemiluminescence is relied upon as an indicator, typical quantities of thymostimulin will range from about 1 ug to about 100 ug/culture. Representative results of experimental determination can be seen in FIG. 1. When visual spreading and/or other biochemical technique(s) which utilize the spreading tendency are employed, typical quantities of thymostimulin or other thymic polypeptide will be about 0.1 mg to about 1.5 mg/culture.

EXAMPLES

Materials and Methods

A. Macrophages

Techniques employed for the harvesting of macrophages are well documented. One typical technique is described below. Mice were sacrificed employing an ether chamber. Animals were injected intraperitoneally with 5 ml of Dulbecco's Modified Eagle's Medium (pH 6.8-7.0), containing a mixture of Penicillin/Streptomycin to control bacterial contamination. The peritoneal cavity was then massaged and the mouse secured so that abdominal skin may be cut and dissected away laterally to reveal the fascia and the peritoneal cavity beneath it. Using a 10 ml syringe with a 19 g needle, the peritoneal fluid was withdrawn from the lateral sides of the cavity and dispensed into disposable centrifuge tubes on ice (to prevent adhesion to the tube). A hemacytometer was utilized to count the total number of peritoneal leukocytes per mouse (macrophages and lyrphocytes). The cells were then centrifuged for ten minutes at 900 rpm, the supernatant fluid decanted and the cells resuspended in DMEM containing antibiotic and ten percent fetal calf serum (heat inactivated) at the desired cell concentration (i.e., 600,000 cells/ml). This suspension is then aliquoted in one ml volumes into the wells of CO-STAR chambers (29 wells, flat bottomed, 16 mm well diameter). The chambers are then incubated in 8% carbon dioxide at 37 degrees C. The cells are usually washed once after 2-4 hour incubation by aspirating the media from the wells and replacing with fresh media. Alternatively, they may be resuspended with phosphate buffered saline (PBS) (pH 7.0-7.2) prior to resuspension.

B. Animals

HRS/J (hr/hr; hr/+) mice (female), average age 8 weeks.

C. Luminol (5-amino-2, 3-dihydro-1 , 4-phthalazinedione, sigma No. A-8511) stock is made up in dimethylsulfoxide ((DMSO) at 12 mg/ml and stored (dark-adapted) for up to 1 month at ambient room temperature. It is currently used at a dilution of 1:7500 for final concentration of $9 \times 10^{-6}$M.

D. Zymosan

S. cerevisiae, (Sigma No..Z-4250) is prepared in Dulbecco's Phosphate Buffered Saline (DPBS), Gibco Laboratories at 15 mg/ml opsonized with fresh human serum and stored in dark adapted containers.

Dulbecco's Phosphate Buffered Saline (DPBS) and Dulbecco's Modified Eagle's Medium (DMEM) (Gibco Labs) utilized in these experiments were also dark-adapted for at least 24 hours prior to use.

F. Scintillation Vials

Twenty ml, borosilicate glass, (Kimble Glass Co.) are tissue culture clean and dark-adapted for at least 24 hr prior to use.

G. Conditions

From the time the cultures are established for initial incubation, all processes are carried out in the dark with only a photographic red light as an illumination source.

H. Macrophage Cultures

Cultures are established according to the previously described method utilizing $2 \times 10^6$ peritoneal leukocytes/well.

I. Chemiluminescence (CL) Procedure:

1. Aliquots (media+cells) in 1 ml amounts are added to scintillation vials and transported in such a manner as to maintain darkness.
2. 0.1 ml of either DPBS (control) or appropriate TP-1 ® concentrations were added to each vial.
3. The cultures were incubated in 6% carbon dioxide at 34 degrees C. for desired time, i.e., 60 min.
4. The cultures were removed from the incubator and returned to the dark room.
5. The cultures were washed twice by aspirating off suspending media, and replacing with DPBS, aspirating, replacing DPBS and washing a final time.
6. The remaining adherent cell population was resuspended in 4.5 ml RPMI + 0.5 ml of appropriate dilution of Luminol (1:7, 500 dilution of a 12 mg/ml stock) to a final concentration of $9 \times 10^{-6}$ M. Note, any combination of dilutions is acceptable as long as the final volume of RPMI + Luminol equals 5 ml and the correct molarity of Luminol is achieved.
7. The cultures were incubated in this reaction mixture for 30 min (6% carbon dioxide at 37 degrees C.).
8. Each vial was cycled through the liquid scintillation counter for a one minute count (Baseline), utilizing the LKB Wallac 1217 Backbeta scintillation counter with a channel operating in the out-of-coincidence mode.
9. Each vial was individually cycled through the counter after which 0.5 ml of opsonized zymosan was added with gentle shaking prior to counting.
10. After each of the nine vials had been counted at zero time with stimulus (opsonized zymosan), all samples were placed in one rack and cycled through every ten minutes. In this manner, one obtains counts at zero time and every ten minutes thereafter.

Controls

The reference standard against which the chemiluminescence values obtained by incubating thymostimulin with macrophage primary cultures are compared and can be any of a variety of suitable materials. Preferred control reagents include fetal calf serum, albumin, heat inactivated thymostimulin, other serum peptides, other extracts of nonlymphoid organ systems, and the like. Fetal calf serum is preferred. Mixtures are operable.

Incubation

In in vitro tests, the incubation of thymostimulin and the macrophage takes place in the presence of suitable quantities of one or more suitable media, such as DMEM, the RPMI series, and the like.

The period of incubation depends upon the nature and quantity of the reagents employed. Generally, incubation times of about 1 hr to about 4 hr are employed.

Phagocytic Stimuli

The chemiluminescent effects brought on by the incubation of TP-1 ® or other suitable source with macrophages in accordance with the invention is made detectable via the use of suitable quantities of one or more phagocytic stimuli. Suitable particulate stimulators include opsonized microorganisms, opsonized zymoson, latex particles, and the like. Suitable stimulators which are soluble include phorbol myristate acetate, a variety of ionophoros, the complement peptide C5a, the fluoride ion, and the like. Opsonized zymoson is preferred. Mixtures are operable.

The observation that thymostimulin exerts substantial effects on two parameters associated with macrophage activation, spreading and chemiluminescent response to phagocytic stimulus, is significant with respect to modulation and/or restoration of macrophage dependent cell-mediated immune reactions. Further, it appears that the HRS/J mouse lends itself as an effective experimental model from which one can routinely evaluate the immuno-potentiating capabilities of thymic hormones and other biological response modifiers.

Reasonable variations, such as those which would occur to a skilled artisan, can be made herein without departing from the scope of the invention.

We claim:

1. A method of assaying the bioactivity of a thymic extract which comprises:
    (a) incubating macrophages derived from the HRS/J mouse with said extract,
    (b) incubating the product of (a) with a phagocytic stimulator,
    (c) adding a luminescent detecting solution to the product of (b),
    (d) measuring the chemiluminescence response of the product of (c), and
    (e) comparing the results obtained in (e) to those obtained using a control extract of known activity.
2. The method of claim 1 wherein the thymic extract is thymostimulin.
3. The method of claim 2 wherein the phagocytic stimulator is opsonized zymosan.
4. The method of claim 3 wherein the luminescent detecting solution comprises luminol.

* * * * *